(12) United States Patent
McNames et al.

(10) Patent No.: US 9,597,015 B2
(45) Date of Patent: Mar. 21, 2017

(54) JOINT ANGLE TRACKING WITH INERTIAL SENSORS

(75) Inventors: James Nathan McNames, Portland, OR (US); Mahmoud El-Gohary, Milwaukie, OR (US); Sean Christopher Pearson, Portland, OR (US)

(73) Assignee: Portland State University, Portland, OR (US)

( * ) Notice: Subject to any disclaimer, the term of this patent is extended or adjusted under 35 U.S.C. 154(b) by 749 days.

(21) Appl. No.: 12/378,486

(22) Filed: Feb. 12, 2009

(65) Prior Publication Data

US 2009/0204031 A1    Aug. 13, 2009

Related U.S. Application Data

(60) Provisional application No. 61/028,118, filed on Feb. 12, 2008.

(51) Int. Cl.
*A61B 5/00*    (2006.01)
*A61B 5/11*    (2006.01)
*A61B 5/107*   (2006.01)

(52) U.S. Cl.
CPC .......... *A61B 5/1121* (2013.01); *A61B 5/1071* (2013.01); *A61B 5/1126* (2013.01); *A61B 5/4528* (2013.01); *A61B 2562/0219* (2013.01)

(58) Field of Classification Search
CPC ... A61B 5/1071; A61B 5/1121; A61B 5/1126; A61B 5/4528; A61B 2562/0219
USPC ........................................................ 600/595
See application file for complete search history.

(56) References Cited

U.S. PATENT DOCUMENTS

| 5,676,157 | A | 10/1997 | Kramer |
| 6,594,617 | B2 | 7/2003 | Scherzinger |
| 7,089,148 | B1 | 8/2006 | Bachmann |
| 7,640,106 | B1 * | 12/2009 | Stokar et al. ................. 701/214 |
| 2008/0285805 | A1 * | 11/2008 | Luinge et al. ................ 382/107 |

OTHER PUBLICATIONS

Zhou, H.; Hu, H.; "Kinematic model aided inertial motion tracking of human upper limb," Proceedings of the 2005 IEEE International Conference on Information Acquisition. pp. 150-155, 2005.*

Wan, E.A.; Van Der Merwe, R.; , "The unscented Kalman filter for nonlinear estimation," Adaptive Systems for Signal Processing, Communications, and Control Symposium 2000. AS-SPCC. The IEEE 2000, pp. 153-158, 2000. doi: 10.1109/ASSPCC.2000.882463.*

(Continued)

*Primary Examiner* — Max Hindenburg
(74) *Attorney, Agent, or Firm* — Mateo Aboy; Aboy & Associates, PC

(57) ABSTRACT

A method for estimating joint angles of a multi-segment limb from inertial sensor data accurately estimates and tracks the orientations of multiple segments of the limb as a function of time using data from a single inertial measurement unit worn at the distal end of the limb. Estimated joint angles are computed from measured inertial data as a function of time in a single step using a nonlinear state space estimator. The estimator preferably includes a tracking filter such as an unscented Kalman filter or particle filter. The nonlinear state space estimator incorporates state space evolution equations based on a kinematic model of the multi-segment limb.

17 Claims, 3 Drawing Sheets

(56) References Cited

OTHER PUBLICATIONS

Zhou et al. "Intertial motion trackign of human arm movements in stroke rehabilition". Proceedings of the IEEE inter. Conf. on Mechatronics and Automation. Jul. 2005. p. 1306-1310.*

Zhu et al. "A real-time articulated human motino tracking using tri-axis intertial/magnetic snesors package". IEEE Trans. on Neural Sys and Rehab Engr. Jun 2004. vol. 12(2): pp. 295-302.*

Kraft, Edgar. "A quaternion-based unscented Kalman filter for orientation tracking." Proceedings of the Sixth International Conference of Information Fusion. vol. 1. 2003.*

Karol J. O'Donovan et al., "An inertial and magnetic sensor based technique for joint angle measurement," Journal of Biomechanics 40 (2007) 2604-2611.

Yaqin Tao et al., "Integration of Vision and Inertial Sensors for Home-based Rehabilitation," Apr. 18, 2005, ICRA'05, IEEE International Conference on Robotics and Automation, Barcelona, Spain.

Yaqin Tao et al., "Integration of Vision and Inertial Sensors for 3D Arm Motion Tracking in Home-based Rehabilitation," The International Journal of Robotics Research vol. 26, No. 6, Jun. 2007, pp. 607-624.

João Luís Marins et al., "An Extended Kalman Filter for Quaternion-Based Orientation Estimation Using MARG Sensors," Proc. of the 2001 IEEE/RSJ International Conference on Intelligent Robots and Systems, Maui, Hawaii, USA, Oct. 29-Nov. 3, 2001.

Daniel Roetenberg et al., "6 DOF Motion Analysis Using Inertial Sensors," Proceedings of Measuring Behavior 2008 (Maastricht, The Netherlands, Aug. 26-29, 2008).

* cited by examiner

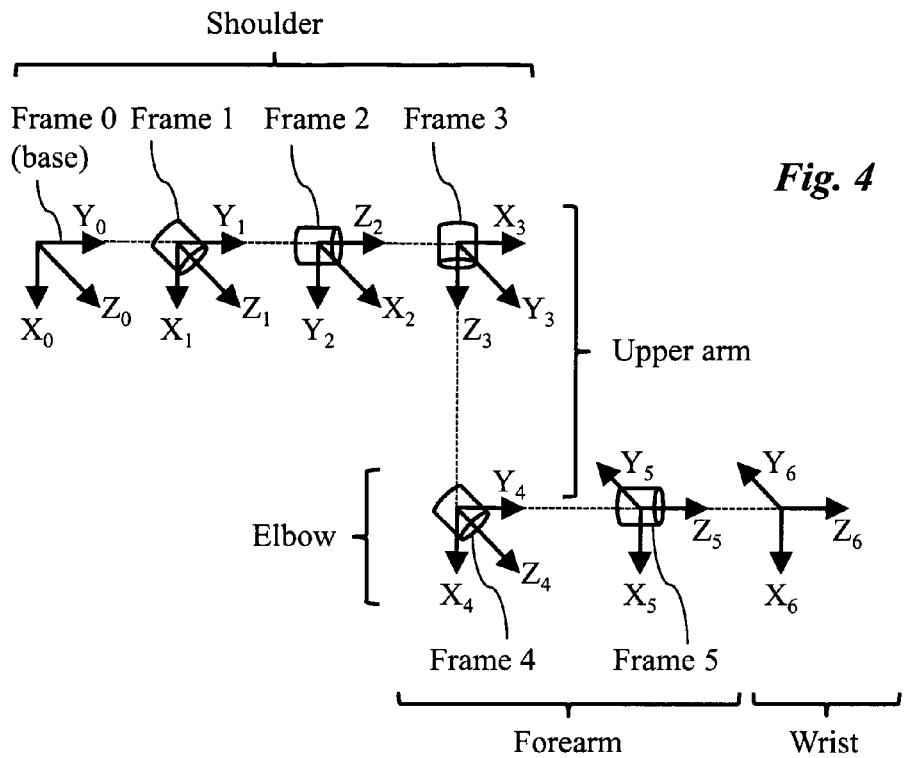
Fig. 4
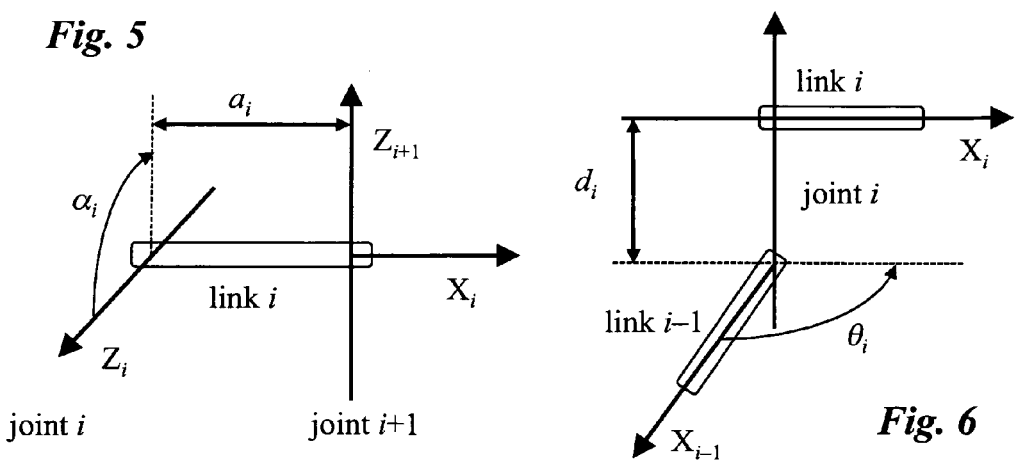
Fig. 5
Fig. 6

JOINT ANGLE TRACKING WITH INERTIAL SENSORS

CROSS-REFERENCE TO RELATED APPLICATIONS

This application claims priority from U.S. Provisional Patent Application No. 61/028,118 filed Feb. 12, 2008, which is incorporated herein by reference.

FIELD OF THE INVENTION

This invention relates generally to methods and devices for estimating and tracking the motion of linkages such as limbs of the human body. More specifically, it relates to improved methods for estimating the motion of a multi-segment linkage using inertial sensors.

BACKGROUND

The measurement and analysis of human movement has many applications including the enhancement of athletic performance, the rehabilitation from injury, and the diagnosis of neurological disorders.

Bodily movements can be measured using a wide variety of techniques and types of sensors. Wearable inertial sensors—which include accelerometers and gyroscopes—enjoy the advantage that they are simple, unobtrusive, and self-contained. They are thus very suitable for continuously recording data over an extended period of time while the the subject performs normal activities of daily life at home. A typical inertial measurement unit (IMU), for example, is a compact wearable device that contains a triaxial accelerometer and/or triaxial gyroscope for measuring movement at a particular position on the body where it is worn. Accelerometers measure the translational acceleration in addition to gravity, and gyroscopes measure angular velocities. An IMU may also contain other types of sensors such as magnetometers. Existing techniques track the movement of a multi-segment limb by placing an IMU at each segment of the limb, e.g., on the shoulder, upper arm, and forearm. Inertial data from the multiple sensors are collected over a period of time, transferred to a computer, and used to estimate the movement of the segments (i.e., their orientations and positions) as a function of time.

Various techniques are known for estimating an orientation of human body segment from inertial data. Traditionally, the orientation of a segment is estimated by integrating the angular velocities measured by gyroscopes, and position is obtained by double integration of the translational acceleration measured by accelerometers. A significant problem with integration, however, is that inaccuracies inherent in the measurements quickly accumulate in the integrated estimation, resulting in an unacceptable levels of integration drift in just a few minutes.

One approach to reducing integration drift is to fuse the gyroscope data with complementary data from magnetometers or other sensors. Increasing the number of sensors helps improve accuracy, but it increases the expense and complexity of the inertial measurement units. It remains a challenge to accurately estimate the state of multiple joints of a limb over extended periods of time with just a few sensors. All known techniques, for example, require a separate inertial sensor unit positioned at each distinct segment of the limb.

A common tracking approach involves applying the Kalman filter for fusing different sensor measurements. However, the linear Kalman filter results in tracking errors when used in a highly nonlinear dynamics. Also, the extended Kalman filter (EKF) is based upon linearizing the state transition and observation matrix with a first-order Taylor expansion, resulting in poor performance when the dynamics are highly nonlinear. The EKF also requires Jacobian matrices and inverse matrix calculation. It also has stability and convergence problems.

In view of the above, there remains a need for improved techniques for accurately tracking the motion of multi-segment limbs for extended periods of time with a small number of sensors.

SUMMARY OF THE INVENTION

In one aspect, the present invention provides an improved technique for estimating joint angles of a multi-segment linkage from inertial sensor data. Surprisingly, the technique is able to accurately estimate and track the orientations of multiple segments of the linkage as a function of time using data from a single inertial measurement unit worn at the distal end of the linkage, thereby reducing expense and increasing ease of use. The single IMU preferably includes a triaxial gyroscope and triaxial accelerometer. The estimation technique is based on a combination of a state space model and tracking filter.

In one embodiment, inertial data is measured as a function of time using a single inertial measurement unit positioned at a distal end of the multi-segment limb of a human body. The single measurement unit preferably includes multiple sensors such as gyroscopes, accelerometers, and/or magnetometers. Estimated joint angles of the multi-segment limb are then computed from the measured inertial data as a function of time in a single step using a nonlinear state space estimator. The estimator preferably includes a tracking filter such as an unscented Kalman filter or particle filter. The nonlinear state space estimator incorporate state space evolution equations based on a kinematic model of the multi-segment limb.

Advantageously, the joint angle estimation technique does not require multiple sensors to track the movement of a limb with multiple segments. It can be used and practiced with various types of inertial sensors. The technique avoids the use of "doublying integrating 3D accelerometer data" and updating a calculation using constraints (fusion steps). Instead, the disclosed technique is executed in a single step that jointly accounts for the kinematic constraints of the segments and the model of the sensors. There is no discrete fusion step required. These and other advantageous features will become apparent in the following description and associated figures.

BRIEF DESCRIPTION OF THE DRAWINGS

FIG. 4 is a schematic diagram illustrating a sequence of coordinate systems used to develop a state space model of an arm used in a method for estimating limb movement according to an embodiment of the invention.

FIG. 5 is a schematic diagram illustrating transformations between two segments in a model of a multi-segment limb used to develop a state space model of an arm used in a method for estimating limb movement according to an embodiment of the invention.

FIG. 6 is a schematic diagram illustrating transformations between two segments in a model of a multi-segment limb used to develop a state space model of an arm used in a method for estimating limb movement according to an embodiment of the invention.

DETAILED DESCRIPTION

Figure 1:
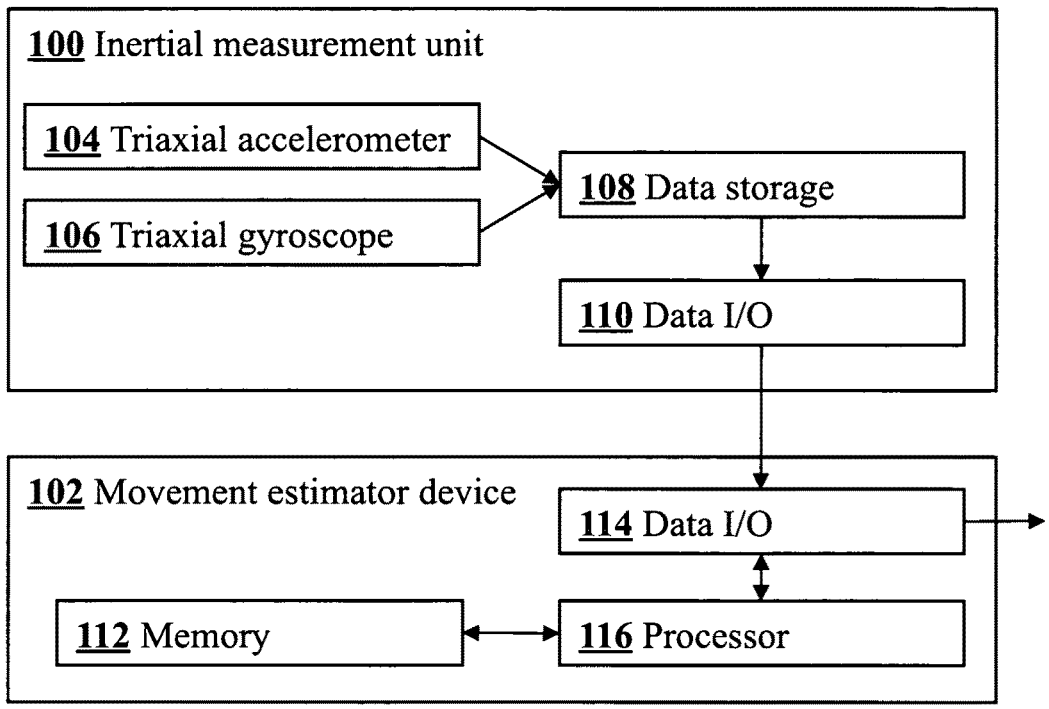
FIG. 1 is a block diagram of a system for estimating limb movement according to an embodiment of the invention.

FIG. 1 is a block diagram of a system for movement estimation according to one embodiment of the invention. The system includes an inertial measurement unit 100 and a movement estimator device 102. Preferably, IMU 100 includes a triaxial accelerometer 104 and triaxial gyroscope 106. In other embodiments, IMU 100 may alternatively or additionally include magnetometers or other sensor types. The sensors 104 and 106 generate inertial data representative of the physical movement of a bodily limb. The data is stored in data storage module 108, such as flash memory. A data input/output component 110 provides an interface to communicate the stored inertial data from the IMU 100 to movement estimator 102, either in real time or off-line via a conventional wired or wireless data link.

Movement estimator 102 includes a memory 112, data input/output interface 114, and processor 116. In one embodiment, movement estimator 102 is a desktop computer. Alternatively, movement estimator 102 may be a networked computer server, in which case the data link from IMU 100 includes a data network and other appropriate intermediate digital communication devices. For example, the data link may include a universal serial bus connection to a desktop computer which is connected to the internet. The inertial data is received at the movement estimator 102 using a data input/output interface 114 and is stored in memory 112 for analysis and motion estimation by processor 116. Motion estimation results, such as position and orientation of limb segments as a function of time, may then be further analyzed and/or provided to other devices through input/output interface 114.

Figure 2:
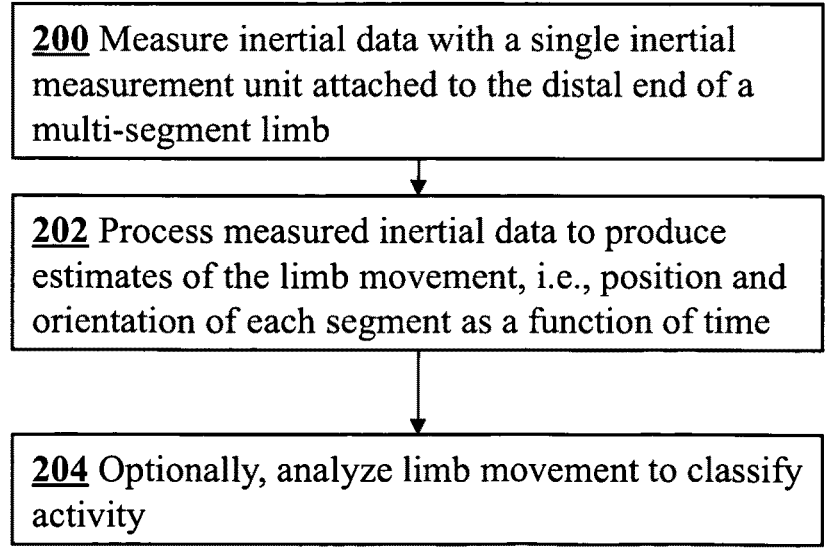
FIG. 2 is a flow chart illustrating a method for estimating limb movement according to an embodiment of the invention.

FIG. 2 is a flowchart illustrating steps of a method according to an embodiment of the invention. In step 200 inertial data is measured using a single inertial measurement unit attached to the distal end of a multi-segment limb of a body. The inertial data is representative of the physical movement of a bodily limb and preferably includes triaxial acceleration data and triaxial angular velocity data. The data may be measured continuously at a predetermined sampling rate over a period of several hours and stored in a memory of the sensor and/or transmitted in periodically or in real time from the sensor to a desktop computer. In step 202, the measured inertial data is processed by a computer to produce estimates of limb movement. The estimates preferably include a temporal sequence of limb segment positions and/or joint angles for each limb segment and joint in the limb. This estimated limb movement data may then be analyzed in step 204 as desired for various application purposes such as activity classification.

In a preferred embodiment, the inertial data is processed using a nonlinear state-space model and unscented Kalman filter for state estimation. The state-space model is derived from a kinematic model of a multi-segment limb. Preferably, in the kinematic model a multi-segment human limb is represented as a kinematic chain, i.e., a sequence of segments connected by joints. Orientation, velocity and acceleration are recursively tracked and propagated from one limb segment to another using Newton-Euler equations for the limb that are implemented in state space form. The tracking filter is preferably an unscented Kalman filter (UKF), which removes the need for linearization and reduces tracking errors by providing estimates that capture the statistics of the target distribution more accurately than EKF. The UKF eliminates the need for Jacobian matrices and the need for inverse matrix calculation in EKF, thereby avoiding stability and convergence problems. This estimation technique can easily handle malfunctions or the loss of some sensor data, and can be used in either a real-time or an off-line processing mode with high accuracy for slow and fast motion.

Kinematic Model

Kinematics refers to the physical laws of motion governing a system without regard to the forces causing the motion. The first step in formulating a kinematic model of a bodily limb is to define a biomechanical model. We focus on the arm and shoulder for the purposes of illustration. A kinematic model is then developed by formulating the propagation of velocity and acceleration in the biomechanical model of the limb.

Figure 3:
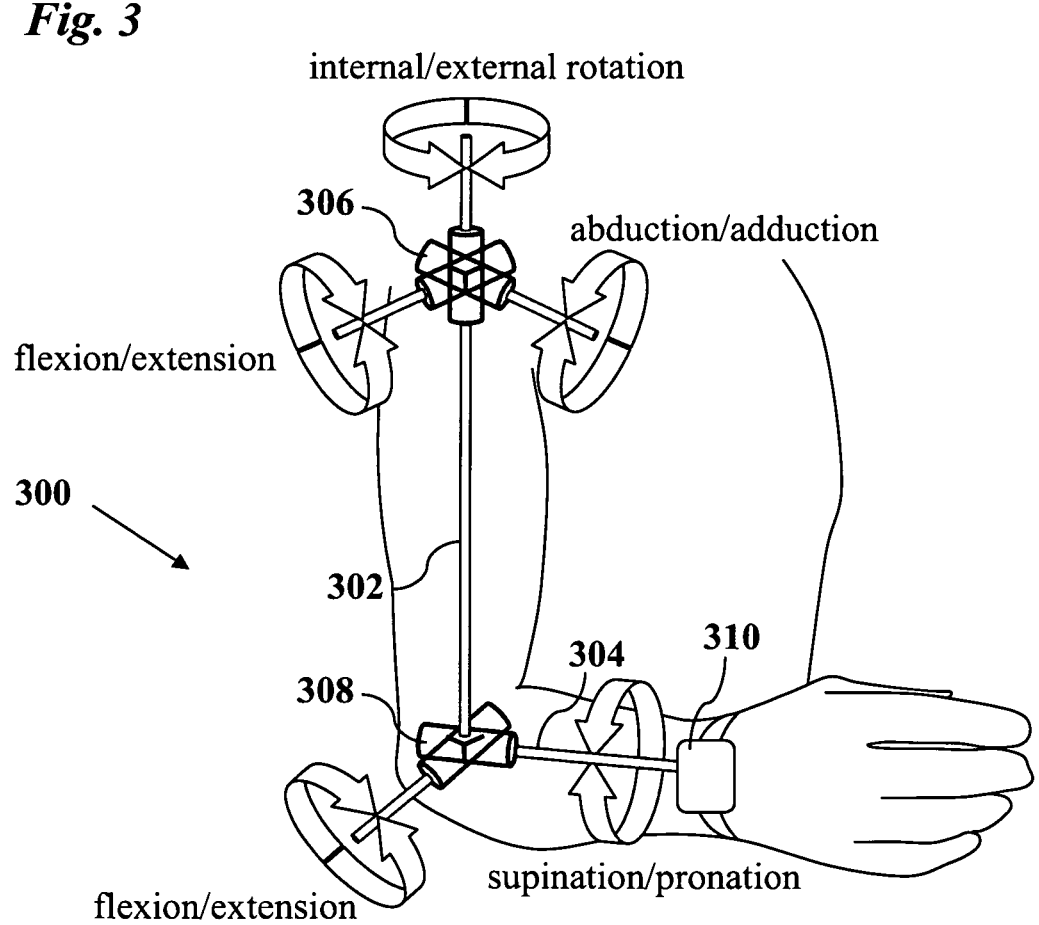
FIG. 3 is an illustration of a biomechanical model of an arm used to develop kinematic state evolution equations used in a method for estimating limb movement according to an embodiment of the invention.

FIG. 3 is an illustration of a biomechanical model of an arm 300 according to an embodiment of the invention. The mechanical functioning of the arm is modeled as a series of multiple rigid segments (or links) connected by joints. This series will also be called a kinematic chain. As shown in the figure, the upper arm is represented by segment 302, the forearm by segment 304, the shoulder by joint 306, and the elbow by joint 308. The shoulder joint 306 is defined as having three degrees of freedom (DOF) corresponding to abduction/adduction, flexion/extension, and internal/external rotation. The elbow joint 308 is defined as having two degrees of freedom corresponding to flexion/extension and pronation/supination. It is convenient to note that a joint with n degrees of freedom is equivalent to n joints of 1 degree of freedom connected by n−1 links of length zero. Thus, the arm model can be described as a sequence of 5 joints with 1 degree of freedom and 5 links where 3 have zero length and 2 have non-zero length. Inertial measurement unit 310 is assumed to be positioned at the distal end of the last segment 304 of the model limb. Since it is positioned on the forearm before the wrist, the wrist and hand are not included in the model.

The position and orientation of each link relative to its neighboring links may be described by defining a coordinate system, or frame, for each link. The position and orientation of one frame is then described with respect to its neighboring links. The following convention may be used to systematically define frames in a kinematic chain:

1. Assign a base coordinate system to some reference, $X_0$, $Y_0$, $Z_0$,
2. Attach a coordinate system to each of the links extending out of the reference; frame $X_i$, $Y_i$, $Z_i$ to link i using the following conventions:
   (a) Align $Z_i$ with the axis of motion of the ith joint,
   (b) Establish $X_i$ along the common normal (perpendicular) of both $Z_i$ and $Z_{i+1}$,
   (c) Establish $Y_i$ to complete the coordinate system according to the righthand rule.
3. For the last link with the n-th frame, assign $X_n$ freely.

The base reference frame does not move and it simplifies calculations to align $Z_0$ along $Z_1$ and to locate the base frame to coincide with the initial position and orientation of the first frame. Similarly, for the last link with the n-th frame, the direction of $X_n$ is chosen so that it aligns with the initial direction of $X_{n-1}$, and the origin of the n-th frame is chosen to coincide with the origin of the (n−1)-th frame to cause as many linkage parameters to become zero. By way of example, FIG. 4 shows the base reference frame at the center of the shoulder joint. Frames 1 through 3 represent shoulder flexion/extension, abduction/adduction and internal/external rotation, respectively. Frames 4 through 5 represent the elbow flexion/extension and pronation/supination of the forearm.

Once the coordinate frames are defined, the next step is to formally relate the coordinate frames to each other. As shown in FIGS. 5 and 6, for each pair of consecutive links, there are four parameters needed to determine the relative location of their respective coordinate frames. The first parameter is the link length $a_i$ which is the shortest distance from $Z_i$ to $Z_{i+1}$ measured along the common normal $X_i$. This is not necessarily the anatomic length of the body segment. It is rather the biomechanical length measured along the common normal of the two axes of rotation. The second parameter is the link twist $\alpha_i$ which is the angle from $Z_i$ to $Z_{i+1}$ measured about the $X_i$ axis. The distance from $X_{i-1}$ to $X_i$ measured along the $Z_i$ axis is known as the link offset $d_i$. The fourth parameter is the joint angle $\theta_i$ and it is the angle from $X_{i-1}$ to $X_i$ measured about the $Z_i$ axis.

Relating these parameters to the arm anatomy, the distance $a_4$ from $Z_3$ to $Z_4$ along the $X_4$ axis is the length of the upper arm $l_u$, and the distance $d_5$ is the length of the forearm $l_f$. See Table 1 for the rest of the D-H parameters.

TABLE 1

Denavit-Hartenberg parameters for the arm model.

| Frame | $\alpha_{i-1}$ | $a_{i-1}$ | $d_i$ | $\theta_i$ |
|---|---|---|---|---|
| 1 | 0 | 0 | 0 | $\theta_1$ |
| 2 | $-\pi/2$ | 0 | 0 | $\theta_2$ |
| 3 | $-\pi/2$ | 0 | 0 | $\theta_3$ |
| 4 | $\pi/2$ | $l_u$ | 0 | $\theta_4$ |
| 5 | $-\pi/2$ | 0 | $l_f$ | $\theta_5$ |

Using the above definitions, the position and orientation of each pair of consecutive links may be described by a combination of rotation and translation transformations that map the configuration of link i to that of link (i−1). Specifically, to relate the i-th frame to the (i−1)-th frame, we perform the following sequence of transformations:

1. Rotate about $X_i$ an angle $\alpha_{i-1}$ to make the two coordinate systems coincide;
2. Translate along $X_i$ a distance $a_{i-1}$ to bring the two origins together;
3. Rotate about $Z_i$ an angle $\theta_i$ to align $X_i$ and $X_{i-1}$;
4. Translate along $Z_i$ a distance $d_{i-1}$ to bring $X_i$ and $X_{i-1}$ into coincidence.

Each of these four transformations may be represented by a 4×4 homogeneous transformation matrix. In particular, we let $R_X$ and $R_Z$ denote rotation matrices about X and Z-axis, respectively, and we let $D_X$ and $D_Z$ denote translation matrices along the X-axis and Z-axis, respectively. The product of these four transformation matrices yields a D-H transformation matrix for adjacent frames i and i−1, $$_i^{i-1}T = R_X(\alpha_{i-1})D_X(a_{i-1})R_Z(\theta_i)D_Z(d_i). \qquad (1)$$

More explicitly, $$_i^{i-1}T = \begin{bmatrix} 1 & 0 & 0 & 0 \\ 0 & \cos(\alpha_{i-1}) & -\sin(\alpha_{i-1}) & 0 \\ 0 & \sin(\alpha_{i-1}) & \cos(\alpha_{i-1}) & 0 \\ 0 & 0 & 0 & 1 \end{bmatrix} \begin{bmatrix} 1 & 0 & 0 & a_{i-1} \\ 0 & 1 & 0 & 0 \\ 0 & 0 & 1 & 0 \\ 0 & 0 & 0 & 1 \end{bmatrix} \times \qquad (2)$$

$$\begin{bmatrix} \cos(\theta_i) & -\sin(\theta_i) & 0 & 0 \\ \sin(\theta_i) & \cos(\theta_i) & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & d_i \\ 0 & 0 & 0 & 1 \end{bmatrix} =$$

$$\begin{bmatrix} \cos(\theta_i) & -\sin(\theta_i) & 0 & a_{i-1} \\ \sin(\theta_i)\cos(\alpha_{i-1}) & \cos(\theta_i)\cos(\alpha_{i-1}) & -\sin(\alpha_{i-1}) & -\sin(\alpha_{i-1})d_i \\ \sin(\theta_i)\sin(\alpha_{i-1}) & \cos(\theta_i)\sin(\alpha_{i-1}) & \cos(\alpha_{i-1}) & \cos(\alpha_{i-1})d_i \\ 0 & 0 & 0 & 1 \end{bmatrix}$$

Now that the biomechanical model of the arm is defined, we use it to formulate the kinematic model of arm movement by considering the velocity and acceleration propagation from link to link. At any instant, each link i of the arm in motion has a linear velocity $v_i$ and an angular velocity $\omega_i$. More precisely, the linear velocity of link i+1 with respect to frame i is denoted $^iv_{i+1}$ and the angular velocity of link i+1 with respect to frame i is denoted $^i\omega_{i+1}$.

The angular velocity of link i+1 is that of link i plus the new velocity component added by joint i+1:

$$^i\omega_{i+1} = {^i\omega_i} + {_{i+1}^iR}\,\dot\theta_{i+1}\,{^{i+1}Z_i}, \qquad (3)$$

where $$\dot\theta_{i+1} = \frac{d}{dt}\theta_{i+1}$$

is the time derivative of $\theta_{i+1}$, and the rotation $_{i+1}^iR$ represents added rotational components due to motion at the joint in frame i. The rotation matrix $_{i+1}^iR$ is derived from the upper left 3×3 block of the D-H matrix shown in equation (2). In the case of the arm model, we have the following rotation matrices are obtained by taking the transpose of the upper left 3×3 D-H transformation matrix in equation (2), and the D-H parameters shown in Table 1

$$_0^1R = \begin{bmatrix} \cos(\theta_1) & \sin(\theta_1) & 0 \\ -\sin(\theta_1) & \cos(\theta_1) & 0 \\ 0 & 0 & 1 \end{bmatrix} \quad _1^2R = \begin{bmatrix} \cos(\theta_2) & 0 & -\sin(\theta_2) \\ -\sin(\theta_2) & 0 & -\cos(\theta_2) \\ 0 & 1 & 0 \end{bmatrix}$$

$$_2^3R = \begin{bmatrix} \cos(\theta_3) & 0 & \sin(\theta_3) \\ -\sin(\theta_3) & 0 & \cos(\theta_3) \\ 0 & -1 & 0 \end{bmatrix} \quad _3^4R = \begin{bmatrix} \cos(\theta_4) & 0 & -\sin(\theta_4) \\ -\sin(\theta_4) & 0 & -\cos(\theta_4) \\ 0 & 1 & 0 \end{bmatrix}$$

$$_4^5R = \begin{bmatrix} \cos(\theta_5) & 0 & \sin(\theta_5) \\ -\sin(\theta_5) & 0 & \cos(\theta_5) \\ 0 & -1 & 0 \end{bmatrix}$$

If we multiply both sides of equation (3) by $_i^{i+1}R$, we obtain the description of the angular velocity of link i+1 with respect to frame i+1:

$$^{i+1}\omega_{i+1} = {_i^{i+1}R}\,{^i\omega_i} + \dot\theta_{i+1}\,{^{i+1}Z_{i+1}}. \qquad (4)$$

The linear velocity of the origin of frame i+1 is the same as that of the origin of frame i plus a new component caused by the rotational velocity of link i:

$$^{i+1}v_{i+1} = {}^{i+1}_i R({}^i v_i + {}^i\omega_i \times {}^i P_{i+1}), \quad (5)$$

where $^i P_{i+1}$ is the position vector of the frame i+1 defined as the upper right 3×1 vector of the D-H matrix shown in equation (2).

The angular acceleration $^{i+1}\dot{\omega}_{i+1}$ from one link to the next is $$^{i+1}\dot{\omega}_{i+1} = {}^{i+1}_i R \, {}^i\dot{\omega}_i + {}^{i+1}_i R \, {}^i\omega_i \times \dot{\theta}_{i+1} \, {}^{i+1}Z_{i+1} + \ddot{\theta}_{i+1} \, {}^{i+1}Z_{i+1}, \quad (6)$$

where $$\ddot{\theta}_{i+1} = \frac{d^2}{dt^2} \theta_{i+1}$$

denotes the second derivative of $\theta_{i+1}$ with respect to time.

The linear acceleration of each link frame origin is $$^{i+1}\dot{v}_{i+1} = {}^{i+1}_i R[{}^i\dot{\omega}_i \times {}^i P_{i+1} + {}^i\omega_i \times ({}^i\omega_i \times {}^i P_{i+1}) + {}^i\dot{v}_i], \quad (7)$$

The equations above are instances of the Newton-Euler equations of motion for the biomechanical model and are summarized in Table 2. They provide a set of forward-recursive equations that propagate linear and angular velocity and acceleration from the reference coordinate system (shoulder) to the last link (wrist).

TABLE 2

Recursive Newton-Euler equations of motion

Forward equations: i = 0, 1, ..., N
$^{i+1}w_{i+1} = {}^{i+1}_i R \, {}^i w_i + \dot{\theta}_{i+1} \, {}^{i+1}Z_{i+1}$
$^{i+1}\dot{w}_{i+1} = {}^{i+1}_i R \, {}^i\dot{w}_i + {}^{i+1}_i R \, {}^i w_i \times \dot{\theta}_{i+1} \, {}^{i+1}Z_{i+1} + \ddot{\theta}_{i+1} \, {}^{i+1}Z_{i+1}$
$^{i+1}\dot{v}_{i+1} = {}^{i+1}_i R[{}^i\dot{w}_i \times {}^i P_{i+1} + {}^i w_i \times ({}^i w_i \times {}^i P_{i+1}) + {}^i\dot{v}_i]$ The initial conditions are $w_0 = \dot{w}_0 = (0, 0, 0)^T$, and $\dot{v}_0 = (g_x, g_y, g_z)^T$, where g is the value of the acceleration due to gravity.

State Space Model

In the case of arm movement tracking using a single inertial measurement unit on the wrist, the state variables are the position $\theta_i(n)$, angular velocity $\dot{\theta}_i(n)$ and acceleration $\ddot{\theta}_i(n)$, where i={1, ..., 5} for the 5 angles of rotation.

The state model equations which describe the evolution of the states with time are given by $$\theta_i(n+1) = \theta_i(n) + T_s\dot{\theta}_i(n) + \frac{1}{2}T_s^2\ddot{\theta}_i(n) \quad (8)$$

$$\dot{\theta}_i(n+1) = \dot{\theta}_i(n) + T_s\ddot{\theta}_i(n) \quad (9)$$

$$\ddot{\theta}_i(n+1) = \alpha\ddot{\theta}_i(n) + u_{\ddot{\theta}_i}(n) \quad (10)$$

where i={1, ..., 5}, $\theta_i(n)$ is the $i^{th}$ angle at time n, $\dot{\theta}_i(n)$ is the angular velocity of the $i^{th}$ angle at time n, $\ddot{\theta}_i(n)$ is the angular acceleration of the $i^{th}$ angle at time n, $u_{\ddot{\theta}_i}(n)$ is a white noise process with zero mean, α is a process model parameter, and $T_s=1/f_s$ is the sampling period. These are standard equations for a physical object traveling at a constant acceleration. In this case the model assumes the acceleration is constant for the duration of a sampling interval, which is typically short enough for this approximation to be sufficiently accurate for tracking. The model of angular acceleration is a first-order autoregressive process with zero mean. Depending on the choice of the parameter α, this represents process models ranging from a random walk model α=1 to a white noise model α=0. Typically the value of α will be assigned an intermediate value that represents typical patterns of human motion in joint angles.

Having defined the kinematic model of the limb, we now formulate the relationship between the measured data and the biomechanical states using a state space model. The general discrete time statistical state-space model is of the form, $$x(n+1)=f_n[x(n),u(n)] \quad (11)$$

$$y(n)=h_n[x(n),v(n)] \quad (12)$$

where n is the discrete time index, where x(n) is the unobserved state of the system, y(n) is the observed or measured data, $f_n[\cdot]$ and $h_n[\cdot]$ are nonlinear state and observation equations, u(n) is process noise, and v(n) is an observation noise. Both u(n) and v(n) are assumed to be white noise with zero mean.

The observation model describes the relationship of the states to the observed data obtained from the inertial measurement unit. The single inertial measurement unit includes a three-axis gyroscope and a three-axis accelerometer. In this case the observation model is given by $$y(n) = \begin{bmatrix} w_x(n) \\ w_y(n) \\ w_z(n) \\ \dot{v}_x(n) \\ \dot{v}_y(n) \\ \dot{v}_z(n) \end{bmatrix} + \begin{bmatrix} v_{gx}(n) \\ v_{gy}(n) \\ v_{gz}(n) \\ v_{ax}(n) \\ v_{ay}(n) \\ v_{az}(n) \end{bmatrix},$$

where $\omega_x$, $\omega_y$ and $\omega_z$ are the angular velocities along the X, Y and Z axes, respectively. The gyroscope noise along the different axes is described by $v_{gx}$, $v_{gy}$ and $v_{gz}$. Similarly, the translational accelerations along the three axes are $\dot{v}_x$, $\dot{v}_y$ and $\dot{v}_z$, and the accelerometer noise along the three axes is given by $v_{ax}$, $v_{ay}$ and $v_{az}$. It should be noted that the acceleration measurement vector includes translational accelerations and the effects of gravity.

Now, the observation equations for the movement of the elbow and forearm are given by $$\omega_x(n)=-[\sin\theta_2(n)]\dot{\theta}_1(n)+v_{gx}(n) \quad (13)$$

$$\omega_y(n)=-[\cos\theta_2(n)]\dot{\theta}_1(n)+v_{gy}(n) \quad (14)$$

$$\omega_z(n)=\dot{\theta}_2+v_{gz}(n) \quad (15)$$

$$\dot{v}_x(n)=-l_f[\cos\theta_2(n)]\dot{\theta}_1(n)+g[\cos\theta_1(n)][\cos\theta_2(n)]+v_{ax}(n) \quad (16)$$

$$\dot{v}_y(n)=l_f[\sin\theta_2(n)]\ddot{\theta}_1(n)-g[\cos\theta_1(n)][\sin\theta_2(n)]+v_{ay}(n) \quad (17)$$

$$\dot{v}_z(n)=-l_f\dot{\theta}_1^2(n)-g[\sin\theta_1(n)]+v_{az}(n), \quad (18)$$

where $\theta_1$ is the elbow flexion/extension angle, and $\theta_2$ is the forearm supination/pronation angle. An analogous approach is used to develop observation equations for the movement of the shoulder and upper arm.

Nonlinear State Estimator

Once the model of the arm is expressed in state space form, any of a variety of nonlinear state space estimation methods can be readily applied to estimate the state from the observed data. Filtering is a common technique of estimating the unobserved state of a dynamic system using a sequence of observations or measurements made on the system. Common filtering methods include the extended Kalman filter (EKF), unscented Kalman filter (UKF), sigma-point Kalman filter (SPKF), or newer methods such as particle filters and their variants. Additionally the EKF, UKF, and SPKF can be used to provide estimates of the state error covariance, thus providing the standard deviations of joint angle estimates. Particle filters provide a means of estimating the entire posterior distribution, providing a direct estimate of any percentile range of estimates without having to assume the distribution is of a specific parametric form, such as Gaussian.

The arm model introduced above exhibits nonlinearities. The use of the linear Kalman filter in a highly nonlinear dynamics introduces estimation errors. The most common approach to solving the nonlinear estimation problem is the extended Kalman filter (EKF) which is based upon linearizing the state and observation models with a first-order Taylor expansion. However, this linearization leads to poor performance if the dynamics are highly nonlinear. Consequently, the unscented Kalman filter is used in a preferred embodiment of the invention. Alternatively, embodiments may use sequential Monte Carlo methods (i.e., particle filters), which are applicable to highly nonlinear and non-Gaussian estimation problems. Particle filters allow for a complete representation of the density function of the unobserved states using a finite number of samples. However, particle filters have a higher computational complexity than unscented Kalman filter, presenting a trade-off between computational cost and estimation accuracy.

The techniques described above may also be applied to a second arm. In addition, each leg can be modeled and tracked with a single sensor on the ankle using the same framework. Consequently, the motion of all four limbs can be tracked with only 4 inertial sensors, and the complete body motion can be tracked with 6 sensors. As anyone with ordinary skill in the art can appreciate, the model is not limited to the joint angles described explicitly herein. For example, other joint angles where the embodiment disclosed can be used directly include the neck, waist, wrist, fingers, and ankles. It can be applied to any series of segments connected by joints. The techniques are capable of tracking joint angles relative to a stationary reference (e.g., a stationary shoulder/chest) or relative to a reference with another sensor (e.g., a moving shoulder/chest with a sensor on it).

Additionally, those of ordinary skill in the art can appreciate that 1) physical limitations of the joint angles can be included to further improve the joint angle estimates; anatomic constraints such as joint natural range of motion imposed by the musculoskeletal system can be integrated in the tracking filter to improve its tracking performance, 2) sensor limitations due to drift or noise can be included in the state space model to improve performance; error models representing sensor drift and noise can be included to obtain improved tracking, 3) an estimate of uncertainty about the estimated joint angles provided by the tracking algorithm can be obtained, 4) the tracking algorithm can provide predicted estimates of the joint angles with decreased accuracy, and 5) the tracking algorithm can provide past and/or smoothed estimates of the joint angles with increased accuracy. The techniques can be applied to any combination of sensors, can easily handle malfunctions or the loss of some sensor inputs, and can be used in either a real-time processing mode or an off-line processing mode with higher accuracy.

As is evident from the above, embodiments of the present invention provide some or all of the following advantages:

The disclosed joint angle estimation technique does not require multiple sensors to track the movement of a limb with multiple segments. This is a significant difference with respect to the closest related art which requires a separate sensor for each segment.

The techniques disclosed herein can be used and practiced with various types of inertial sensors that are available. This advantage also represents a significant difference with respect to existing methods.

As more sensors are added, the tracking performance improves.

The disclosed technique does not use "doublying integrating 3D accelerometer data" or updating a calculation using constraints (fusion steps). Instead, the disclosed technique is executed in a single step that jointly accounts for the kinematic constraints of the segments and the model of the sensors. There is no discrete fusion step required.

The disclosed technique does not require 3D accelerometer and 3D angular velocity sensor data.

What is claimed is:

1. A method for estimating and tracking joint angles of a human multi-segment linkage, the method comprising:
    a) measuring inertial data as a function of time using an inertial measurement unit positioned at a distal end of the human multi-segment linkage; and
    b) computing from the measured inertial data estimated joint angles of the human multi-segment linkage as a function of time using a nonlinear state space estimator including an observation model incorporating an acceleration measurement vector comprising both translational accelerations and gravitational effects.

2. The method of claim 1 wherein said measurement unit includes multiple sensors, wherein each of the multiple sensors is selected from the group consisting of a gyroscope, an accelerometer, and a magnetometer.

3. The method of claim 1 wherein said inertial measurement unit includes a triaxial gyroscope and triaxial accelerometer.

4. The method of claim 1 wherein the nonlinear state space estimator comprises a tracking filter selected from the group consisting of an unscented Kalman filter and a particle filter.

5. The method of claim 1 wherein the nonlinear state space estimator comprises state space evolution equations based on a kinematic model of the multi-segment linkage.

6. The method of claim 1 wherein the nonlinear state space estimator comprises state space evolution equations that incorporate physical limitations of the joint angles.

7. The method of claim 1 wherein the nonlinear state space estimator comprises observation equations that incorporate sensor measurement noise.

8. The method of claim 1 wherein the nonlinear state space estimator computes an estimate of uncertainty of the estimated joint angles.

9. The method of claim 1 wherein the nonlinear state space estimator computes predicted estimates of the joint angles.

10. The method of claim 1 wherein the nonlinear state space estimator computes smoothed estimates of the joint angles.

11. The method of claim 1 wherein the multi-segment linkage is a human limb.

12. A system for estimating joint angles of a human multi-segment linkage, the system comprising:

a) an inertial measurement unit for measuring inertial data as a function of time from a distal segment of the human multi-segment linkage;
b) a memory for storing the measured inertial data; and
c) a nonlinear state-space estimator including an observation model incorporating an acceleration measurement vector comprising both translational accelerations and gravitational effects implemented in a computer for estimating from the measured inertial data the joint angles of the human multi-segment linkage as a function of time.

13. The system of claim 12, wherein said single measurement unit includes multiple sensors, wherein each of the multiple sensors is selected from the group consisting of a gyroscope, an accelerometer, and a magnetometer.

14. The system of claim 12 wherein said single inertial measurement unit includes a triaxial gyroscope and triaxial accelerometer.

15. The system of claim 12 wherein the nonlinear state space estimator comprises a tracking filter selected from the group consisting of an unscented Kalman filter and a particle filter.

16. The system of claim 12 wherein the nonlinear state space estimator comprises state space evolution equations based on a kinematic model of the multi-segment linkage.

17. The system of claim 12 wherein the multi-segment linkage is a human limb.

* * * * *